United States Patent

Ross et al.

[11] 4,134,917
[45] Jan. 16, 1979

[54] METHOD FOR THE DENITROSATION OF ORGANIC NITROSAMINES

[75] Inventors: Lawrence J. Ross, Martinsville; George A. Chiarello, Trenton, both of N.J.

[73] Assignee: American Cyanamid Company, Stamford, Conn.

[21] Appl. No.: 790,375

[22] Filed: Apr. 25, 1977

[51] Int. Cl.² ............................................. C07C 85/11
[52] U.S. Cl. .................................... 260/577; 71/121; 260/563 R; 260/563 C; 260/563 P; 260/571; 260/573; 260/574; 260/576; 260/583 R; 260/584 C
[58] Field of Search ................ 260/577, 583 CC, 647, 260/576, 583 R, 571, 563 R, 574

[56] References Cited

U.S. PATENT DOCUMENTS

| | | | |
|---|---|---|---|
| 2,419,718 | 4/1947 | Kehe | 260/576 |
| 4,034,042 | 7/1977 | Wedemeyer et al. | 260/576 |

FOREIGN PATENT DOCUMENTS

| | | | |
|---|---|---|---|
| 542408 | 6/1957 | Canada | 260/583 CC |
| 41-1235 | 1/1966 | Japan | 260/576 |

OTHER PUBLICATIONS

Sidgwick, "The Organic Chemistry of Nitrogen", 3'd Ed, pp. 592–594 (1966).
Biggs et al., "J. Chem. Soc., Perkin Trans II", pp. 601–605 (1976).
Biggs et al., "J. Chem. Soc., Perkin Trans II", pp. 107–111 (1975).

*Primary Examiner*—Winston A. Douglas
*Assistant Examiner*—John Doll
*Attorney, Agent, or Firm*—H. G. Jackson

[57] ABSTRACT

The invention relates to a method for the denitrosation of organic nitrosamines with aliphatic and cycloaliphatic ketones or aliphatic aldehydes in the presence of a strong acid, and optionally an inert organic solvent.

9 Claims, 1 Drawing Figure

NITRATING COMPOSITION

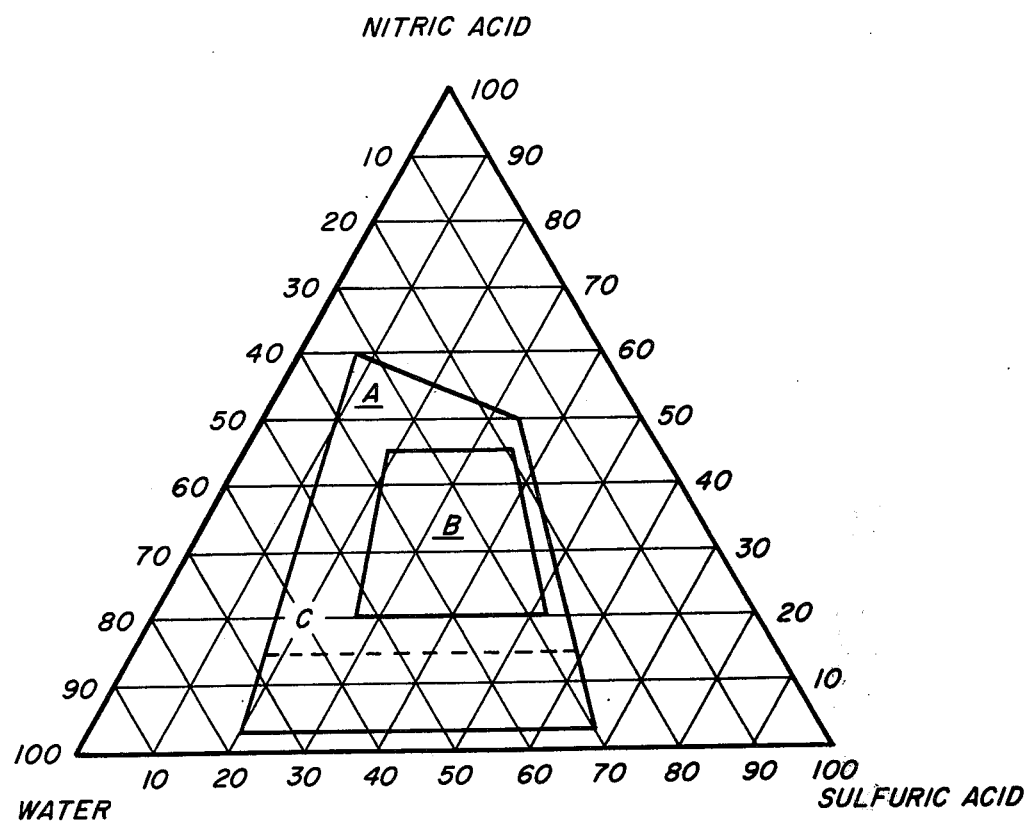

METHOD FOR THE DENITROSATION OF ORGANIC NITROSAMINES

N-nitrosamines can result from the action of nitrosating agents on secondary amines. These conditions prevail in a wide variety of commercial chemical processes, and under less obvious conditions such as the use of nitrate salts as corrosion inhibitors for products which contain secondary amines. A considerable number of N-nitrosamines have been found to be carcinogenic in tests with laboratory animals. This invention provides a novel and useful procedure for the irreversible decomposition of such nitrosamines so that their concentrations in the final product may be reduced to low levels.

This invention also finds utility in other cases where decomposition of a nitrosamine will result in improved yield of a desired product. For example, it is known that in the course of nitrating an aromatic amine of formula (II), in addition to obtaining the desired dinitroanilines of formula (I), N-nitrosanilines of formula (III):

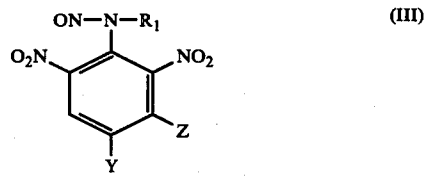

wherein $R_1$ is alkyl $C_1$-$C_6$ (straight chain or preferably branched), cycloalkyl $C_4$-$C_6$, monohaloalkyl $C_1$-$C_4$ or alkoxy($C_1$-$C_4$)alkyl ($C_2$-$C_4$), Y Y is alkyl $C_{1-C4}$ or $CF_3$ Z is hydrogen, halogen, alkyl $C_1$-$C_4$, alkoxy $C_1$-$C_4$, monohaloalkyl $C_1$-$C_4$ or alkoxy($C_1$-$C_4$)alkyl($C_2$-$C_4$), are also formed in the course of the nitration reaction. Obviously, formation of these N-nitroso compounds results in lowering the yields of the desired formula (I) herbicidal dinitroanilines. The overall yields of the desired formula (I) compounds can be improved, however, by subjecting the undesired formula (II) N-nitrosoanilines to a denitrosation reaction.

The state of the art of denitrosations is described by Ian D. Briggs et al. in *J. Chem. Soc. Perkin* II, page 601ff (1976).

One of the most often used denitrosating agents is sulfamic acid, used in conjunction with strong acids, such as hydrochloric acid. The method of denitrosating with sulfamic acid, while effective, has certain undesirable features. Relatively large molar excesses of sulfamic acid are usually required per mole of N-nitroso compound with the concomitant use of large molar amounts of a strong acid (e.g. HCl). Additionally, the denitrosation reaction with sulfamic acid is highly exothermic, and since in the course of the reaction nitrogen gas is evolved, the reaction requires the use of pressure reactors capable of withstanding relatively high superatmospheric pressures, or else the reactor requires periodic venting to relieve excess pressure. Such venting usually results in the loss of solvents (if used) and volatile acid along with the nitrogen, both of which must then be replenished. Furthermore, on a large scale, the addition of solid sulfamic acid to a reactor is cumbersome, and precise metering (to control the exotherm or to permit continuous operation) is difficult. Finally, since the product is usually isolated from the reaction mixture by adjusting the pH of the reaction mixture to neutral or alkaline with a base, such as sodium hydroxide, these highly acidic mixtures require the use of large amounts of base.

Surprisingly, we now find that by the denitrosation method of the invention, N-nitrosoamines of formula (IV):

wherein R' represents (among others) alkyl $C_1$-$C_{12}$ (straight chain or branched), cycloalkyl $C_4$-$C_8$, haloalkyl $C_1$-$C_{10}$, alkoxy ($C_1$-$C_6$)alkyl($C_1$-$C_8$), phenyl or substituted phenyl, wherein the substituents may be one or more of the following: halogen, alkyl $C_1$-$C_4$ (straight chain or branched), alkoxy $C_1$-$C_4$, trifluoromethyl, alkoxy($C_1$-$C_4$)alkyl($C_1$-$C_4$) or nitro; R" represents alkyl $C_1$-$C_8$ (straight chain or branched), cycloalkyl $C_4$-$C_8$, monohaloalkyl $C_1$-$C_6$ or alkoxy($C_1$-$C_4$)alkyl($C_1$-$C_4$); and N-nitroso-dinitroanilines of formula (III):

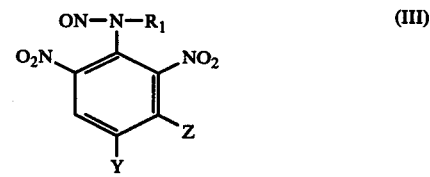

wherein $R_1$, Y and Z are as hereinabove defined; in particular, can be efficiently denitrosated with aliphatic and cycloaliphatic ketones or aliphatic aldehydes in the presence of a strong acid, preferably one which contains a good nucleophilic anion, such as hydrochloric or hydrobromic acid. The ketones and aldehydes can be represented by formulae:

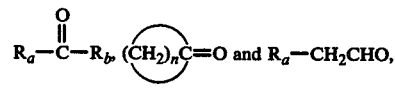

wherein $R_a$ is phenyl; substituted phenyl, or lower alkyl; and $R_b$ is lower alkyl, and wherein the substituent(s) are from one or two of $C_1$-$C_4$ alkyl, $C_1$-$C_4$ alkoxy or halogen; and n is an integer from the numbers 3 to 7.

Illustrative of the ketones and aldehydes which can be utilized in this procedure are: acetone, methyl ethyl ketone, diethyl ketone, diisopropyl ketone, di-n-butyl ketone, methyl phenyl ketone, ethyl phenyl ketone, methyl-p-tolyl ketone, methyl-p-chlorophenyl ketone, methyl p-methoxyphenyl ketone, cyclopentanone, cyclohexanone, cycloheptanone, acetaldehyde, propionaldehyde, butyraldehyde, benzaldehyde, p-chlorobenzaldehyde, 2,4-dimethoxybenzaldehyde, p-tolualdehyde, and the like.

Illustrative of the nitrosamines which can be decomposed by this procedure are:

N,N-dimethyl-N-nitrosamine;
N,N-diethyl-N-nitrosamine;
N,N-dipropyl-N-nitrosamine;
N-ethyl-N-propyl-N-nitrosamine;
N,N-dihydroxyethyl-N-nitrosamine;
N-(1-methylpropyl)-N-nitroso-2,6-dinitro-3,4-xylidine;
N-(1-ethylpropyl)-N-nitroso-2,6-dinitro-3,4-xylidine.

Advantageously, a formula (III) N-nitrosoamine is denitrosated by the novel method of the present invention as follows:

One molar equivalent of a formula (III) compound is dissolved in an inert solvent selected from chlorinated hydrocarbons, such as chloroform, carbon tetrachloride, ethylene dichloride, and the like, aliphatic or aromatic hydrocarbons and lower alcohols. To the thus-obtained solution, 0.5 to 10 moles, and preferably 2 to 6 moles of a strong acid, such as hydrochloric acid, is added. Next, a ketone or an aldehyde, of the above defined group of ketones and aldehydes is added to the above mixture, in a ratio of 0.5 to 2 moles, and preferably 0.75 to 1.5 moles per mole of N-nitroso compound; although larger than the above-defined amounts may be used, if so desired (e.g. the ketone and aldehyde may be used as reactant/solvent). The reaction may be conducted at atmospheric pressure, but is preferably conducted at superatmospheric pressures not more than 100 psig, at a temperature range of 20° C. to 120° C., and preferably 80° C. to 110° C. When the reaction is conducted at atmospheric pressure, some of the volatile acid and solvent is usually lost to the environment, thus requiring periodic addition of both to the reaction mixture to compensate for the losses. The denitrosation reaction is temperature related; i.e., at about 20°-60° C., the reaction time is in excess of 24 hours, while at 105°-110° C. the reaction is complete in about one hour's time.

We find, that the novel denitrosation reaction of the present invention offers certain advantages over conventional denitrosating agents, such as sulfamic acid. Generally, the ketones and aldehydes are used at lower molecular ratios and thus are less expensive. Additionally, depending on the ketone or aldehyde selected, they can be less toxic and thus safer to handle; moreover, being liquids, their addition to the reaction mixture can be more easily controlled, and metered, if necessary, to so regulate the denitrosation reaction. Significantly, denitrosation with the ketones and aldehydes is less exothermic, and the pressure build-up is significantly reduced so that temperature and pressure control within the reactor is more easily achieved. A further advantage of the novel process of the present invention is, that by using the above-described ketones and aldehydes, less acid is needed to promote the reaction; and therefore, ultimately less base is required to neutralize the acids, as well as the sulfamic and sulfuric acids, in the course of the isolation of the products represented by formula (I). Typical denitrosations by the novel process of the present invention are given in the examples below, showing the denitrosation of N-(1-ethylpropyl)-N-nitroso-2,6-dinitro-3,4-xylidine (of formula III) to the corresponding N-(1-ethylpropyl)-2,6-dinitro-3,4-xylidine (of formula I) in an ethylene dichloride solution containing both of the above-identified compounds, wherein the ethylene dichloride solution was obtained by a preferred nitration process, referred to above and described below in detail, as follows:

Compounds of formula (I):

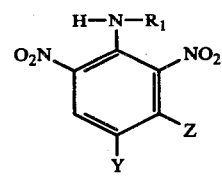

wherein $R_1$ represents alkyl $C_1$–$C_6$ (straight chain or preferably branched), cycloalkyl $C_4$–$C_6$, monohaloalkyl $C_1$–$C_4$ or alkoxy($C_1$–$C_4$)alkyl($C_2$–$C_4$); Y represents alkyl $C_1$–$C_4$, halogen or $CF_3$; Z represents hydrogen, halogen, alkyl $C_1$–$C_4$, alkoxy $C_1$–$C_4$, monohaloalkyl $C_1$–$C_4$ or alkoxy($C_1$–$C_4$)alkyl($C_2$–$C_4$) can be efficiently prepared by nitrating a compound of formula (II):

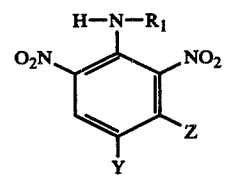

wherein $R_1$, Y and Z are as hereinabove defined, and V and W are hydrogen or nitro, provided that V and W are not both nitro, in a three component mixed acid nitration mixture [hereinafter also referred to as mixed acid(s)] defined below. The nitrating agents employed are graphically represented by the Trapezium A, set forth in FIG. 1; that is, compositions within the area defined by the lines connecting the points corresponding to: 60% $HNO_3$, 8% $H_2SO_4$ 32% $H_2O$; 50% $HNO_3$, 35% $H_2SO_4$, 15% $H_2O$; 2% $HNO_3$, 68% $H_2SO_4$, 30% $H_2O$; and 2% $HNO_3$, 20% $H_2SO_4$, 78% $H_2O$. Each of these values represents a real weight percent. A more preferred three component nitrating composition fall within the Trapezium C, shown in the FIGURE. That is the area encompassed by the lines and the dotted line connecting the points corresponding to: 60% $HNO_3$, 8% $H_2SO_4$, 32% $H_2O$; 50% $HNO_3$, 35% $H_2SO_4$, 15% $H_2O$; 15% $HNO_3$, 17% $H_2SO_4$, 68% $H_2O$; and 15% $HNO_3$, 58% $H_2SO_4$, 27% $H_2O$. The most preferred three component nitrating composition fall within the Trapezoid B, shown in the FIGURE; that is the area encompassed by the lines connecting the points corresponding to 45% $HNO_3$, 19% $H_2SO_4$, 36% $H_2O$; 45% $HNO_3$, 36% $H_2SO_4$, 19% $H_2O$; 20% $HNO_3$, 52% $H_2SO_4$, 28% $H_2O$; and 20% $HNO_3$, 27% $H_2SO_4$, 53% $H_2O$.

The optimum number of moles of nitric acid per mole of formula (II) compound will depend on the compound to be nitrated and the composition of the nitric acid used. In general, formula (II) compounds, wherein V and W are both hydrogen, are nitrated using from 2.5 to 5.0 moles, and preferably 2.5 to 3.5 moles of nitric acid per mole of the compound. Formula (II) compounds, wherein V or W is nitro, are nitrated using from 1.2 to 4.0 moles, and preferably 1.5 to 2.5 moles of nitric acid per mole of the compound.

The mole ratio of sulfuric acid to formula (II) compound being nitrated may range from 1.5 to 15 moles, and preferably 2 to 10 moles (of acid) per mole of the compound. On a weight percentage basis, these ranges of sulfuric acid correspond to from about 30% to 70%, preferably 35% to 65%.

The amount of water present in the mixed acids is an important factor and is related to the optimum temperature of the nitration reaction. In general, reaction mixtures which contain higher percentages of water, require higher reaction temperatures. The amount of water in the starting nitration mixture should be from about 15% to about 78% on the weight of the nitration mixture. A sufficiently high temperature should be employed to convert any N-alkyl mononitroaniline (of formula II) to the desired dinitroaniline. Compounds of formula (II) can be nitrated at temperatures of from 0° C. to 70° C.; however, temperatures below 15° C. tend to hinder completion of the dinitration and are thus not the most desirable. Temperatures above 70° C. are not desirable, because the reaction becomes difficult to control. The reaction is exothermic and cooling is generally required to maintain the temperature below the upper limit and desirably within the optimum range. The optimum temperature will vary depending on the formula (II) amine to be nitrated and the composition of the mixed acid. The generally preferred reaction temperature range is from about 35° C. to about 60° C.

When operating in the range of 0° C. to 70° C., and preferably 35° C., to 60° C., the nitration with mixed acids is easily controlled.

An additional advantage of nitrating with a mixed acid is that only a small excess (0.5 to 1.5 mole) of nitric acid is necessary to complete the reaction. With concentrated nitric acid, at least 5 to 10 moles would be required. The cost and potential hazard with concentrated nitric acid would be far greater than with mixed acids, where nitric acid recovery is not essential to the economics of the process.

Compounds of formula (II) may be reacted with the nitration mixture as liquids, solids or dissolved in an inert solvent, such as ethylene dichloride, chloroform, carbon tetrachloride, nitromethane, and the like, preferably in ethylene dichloride.

The mode of action is not critical; the nitrating agent (mixed acid) may be added to the starting compound of formula (II), or the compound may be added to the nitrating agent, depending on the particular situation.

As stated above, in the course of nitrating a formula (II) compound, e.g. N-(1-ethylpropyl)-3,4-xylidine to obtain the desired N-(1-ethylpropyl)-2,6-dinitro-3,4-xylidine herbicide, as a by-product, N-(1-ethylpropyl)-N-nitroso-2,6-dinitro-3,4-xylidine [a compound of formula (II)] is also obtained in appreciable yields. Thus, it is of obvious advantage to denitrosate this compound, since denitrosation results in increasing product yields by approximately the N-(1-ethylpropyl)-N-nitroso-2,6-dinitro-3,4-xylidine by-product present.

Conveniently, when the nitration is conducted in the presence of an inert solvent (e.g. ethylene dichloride), at completion of the reaction both of the above referred to compounds are present, dissolved in the solvent, and upon separation of the organic layer from the spent aqueous nitration acid, the former may be used as is in the novel denitrosation method of the present invention.

The novel method of the invention is further illustrated in the examples below, which are not to be taken as being limitative thereof.

EXAMPLE 1

Denitrosation of N-(1-Ethylpropyl)-N-nitroso-2,6-dinitro-3,4-xylidine with diethyl ketone A glass pressure reactor is charged with an ethylene dichloride solution (96.0 g) containing N-(1-ethylpropyl)-2,6-dinitro-3,4-xylidine (38.2% by weight) and N-(1-ethylpropyl)-N-nitroso-2,6-dinitro-3,4-xylidine (13.4% by weight), concentrated hydrochloric acid (14.7 g) and diethyl ketone (2.50 g), and the reactor is then sealed. The reaction mixture is heated to 80°-85° C. and stirred for 4 hours while the temperature is maintained at 80°-85° C. The pressure rose to a maximum of 24 psig and then fell slowly to 18 psig in the course of the reaction. At the end of the reaction, the reactor is cooled down, vented, and the reaction mixture contained therein is adjusted to pH 10 and 10% sodium hydroxide, and filtered. The filter cake is washed several times with ethylene dichloride, the organic layer is separated, and the solvent removed under reduced pressure to afford 51.4 g solid, which contains (by analysis) 93.3% by weight of N-(1-ethylpropyl)-2,6-dinitro-3,4-xylidine and <0.01% by weight of N-(1-ethylpropyl)-N-nitroso-2,6-dinitro-3,4-xylidine.

EXAMPLE 2

Denitrosation of N-(1-Ethylpropyl)-N-nitroso-2,6-dinitro-3,4-xylidine with sulfamic acid A glass pressure reactor is charged with an ethylene dichloride solution (96.0 g) containing N-(1-ethylpropyl)-2,6-dinitro-3,4-xylidine (38.2% by weight) and N-(1-ethylpropyl-N-nitroso-2,6-dinitro-3,4-xylidine (13.4% by weight), concentrated hydrochloric acid (14.7 g) and sulfamic acid (6.48 g), and the reactor is then sealed. The reaction mixture is heated to 80°-85° C. and stirred for 4 hours while the temperature is maintained at 80°-85° C. The pressure rose to 80+ psig, and the reactor is vented periodically in the course of the reaction in order to maintain the internal pressure within safe operating limits. At the end of the reaction, the reactor is cooled down and vented, and the reaction mixture contained therein is adjusted to pH 10 with 10% sodium hydroxide and filtered. The filter cake is washed several times with ethylene dichloride, the organic layer is separated and the solvent removed under reduced pressure to afford 52.15 g solid, which contains (by analysis) 89.9% by weight of N-(1-ethylpropyl)-2,6-dinitro-3,4-xylidine and <0.01% by weight of N-(1-ethylpropyl)-N-nitroso-2,6-dinitro-3,4-xylidine.

EXAMPLE 3

Denitrosation of N-(1-Ethylpropyl)-N-nitroso-2,6-dinitro-3,4-xylidine with diethyl ketone Diethyl ketone (20 gal) is charged to a blend tank containing an ethylene dichloride solution (890 gal) of N-(1-ethylpropyl)-2,6-dinitro-3,4-xylidine (about 40% by weight of solution) and N-(1-ethylpropyl)-N-nitroso-2,6-dinitro-3,4-xylidine (about 15% by weight of solution). A 2000-gallon pressure reactor is charged with about one-fourth of the above blend tank mixture, concentrated hydrochloric acid (124 gal) is added, and the reactor is then sealed. The reaction mixture is stirred and heated to 85°-90° C., and the remainder of the contents of the blend tank is added over 35 minutes. Pressure is maintained at approximately 30 psig by periodically venting the reactor. After the addition of the blend tank mixture is completed, samples are periodically withdrawn from the reactor, worked up by the procedures described in Examples 1 and 2, and analyzed to determine the degree of denitrosation achieved. The data obtained are summarized in Table I appended herein.

TABLE I

Analytical Data, Showing the Degree of Denitrosation Achieved in the Above reaction.

| Sample | Sample Taken, Hours After Reaction Began | Found % A* | % B* |
|---|---|---|---|
| 1 | 0 | 91.2 | 1.3 |
| 2 | 1 | 90.6 | 0.06 |
| 3 | 2 | 91.2 | 0.006 |
| 4 | 3 | 90.1 | 0.003 |
| 5 | 4 | 91.3 | <0.003 |

*Wherein:
A = N-(1-ethylpropyl)-2,6-dinitro-3,4-xylidine
B = N-(1-ethylpropyl)-N-nitroso-2,6-dinitro-3,4-xylidine.

It can be clearly seen from the above table that the amount of N-(1-ethylpropyl)-N-nitroso-2,6-dinitro-3,4-xylidine present in the reaction mixture is substantially decreased as the reaction time is increased.

EXAMPLE 4

Determination of the Effect of the Molar Ratios of Diethyl Ketone to N-(1-Ethylpropyl)-N-nitroso-2,6-dinitro-3,4-xylidine on the Denitrosation Reaction The following experiment serves to determine the effect of various amounts of diethyl ketone used to denitrosate N-(1-ethylpropyl)-N-nitroso-2,6-dinitro-3,4-xylidine (B) to the corresponding N-(1-ethylpropyl)-2,6-dinitro-3,4-xylidine (A).

PROCEDURE

A glass pressure reactor is charged with N-(1-ethylpropyl)-N-nitroso-2,6-dinitro-3,4-xylidine (2.88 g), concentrated hydrochloric acid (2.94 g), the appropriate amount of diethyl ketone and ethylene dichloride (20 ml), and the reactor is then sealed. The reaction mixture is heated to 80°–85° C. over 30 minutes and stirred 4 hours while maintaining the temperature at 80°–85° C. At the end of the reaction, the reactor is cooled down and vented. Thin-layer chromatography of the crude reaction mixtures indicates the presence of only small amounts of compound B. The reaction mixtures are worked up by the procedures of Examples 1 and 2 and the solid residues are analyzed. The data obtained are summarized in Table II appended hereto.

TABLE II

The Effect of the Molar Ratio of Diethyl Ketone (DEK) to N-(1-Ethylpropyl)-N-nitroso-2,6-dinitro-3,4-xylidine on the Denitrosation of Same

| Sample | Moles of DEK* per Mole of B | Found % A* | % B* |
|---|---|---|---|
| 1 | 1 | 82.6 | 0.012 |
| 2 | 0.5 | 77.3 | 4.0 |
| 3 | 0.25 | 73.3 | 8.0 |

*Wherein:
DEK = Diethyl ketone
A = N-(1-Ethylpropyl)-2,6-dinitro-3,4-xylidine
B = N-(1-Ethylpropyl)-N-nitroso-2,6-dinitro-3,4-xylidine

EXAMPLE 5

Denitrosation of N-(1-Ethylpropyl)-N-nitroso-2,6-dinitro-3,4-xylidine with propionaldehyde A glass pressure reactor is charged with an ethylene dichloride solution (19.2 g) containing N-(1-ethylpropyl)-2,6-dinitro-3,4-xylidine (about 40% by weight) and N-(1-ethylpropyl)-N-nitroso-2,6-dinitro-3,4-xylidine (about 15% by weight), concentrated hydrochloric acid (2.94 g) and propionaldehyde (1.0 g), and then the reactor is sealed. The reaction mixture is heated to 80°–85° C. over 30 minutes and stirred for 4 hours while the temperature is maintained at 80°–85° C. In the course of the reaction very little pressure buildup is observed. At the end of the reaction, the reactor is cooled down, vented, and the reaction mixture contained therein is adjusted to pH 10+ with 12% sodium hydroxide. The mixture is filtered, the filter cake washed several times with ethylene dichloride. The organic layer is separated and is analyzed. The organic layer is found to contain 30% by weight of N-(1-ethylpropyl)-2,6-dinitro-3,4-xylidine and only 0.7% by weight of N-(1-ethylpropyl)-N-nitroso-2,6-dinitro-3,4-xylidine.

EXAMPLE 6

Denitrosation of N-(1-Ethylpropyl)-N-nitroso-2,6-dinitro-3,4-xylidine with acetone A glass pressure reactor is charged with an ethylene dichloride solution (96.0 g) containing N-(1-ethylpropyl)-2,6-dinitro-3,4-xylidine (40.9% by weight) and N-(1-ethylpropyl)-N-nitroso-2,6-dinitro-3,4-xylidine (14.4% by weight), concentrated hydrochloric acid (14.7 g) and acetone (2.50 g), and the reactor is then sealed. The reaction mixture is heated to 80°–85° C. and stirred for 4 hours while the temperature is maintained at 80°–85° C. The pressure rose to 32 psig and remained constant during the entire reaction time. At the end of the reaction, the reactor is cooled down, vented and the reaction mixture contained therein is adjusted to pH 10.5 with 12% sodium hydroxide and filtered. The filter cake is washed several times with ethylene dichloride, the organic layer is separated and the solvent removed under reduced pressure to afford 53.78 g of solid, which contains (by analysis) 91.1% by weight of N-(1-ethylpropyl)-2,6-dinitro-3,4-xylidine and 0.02% by weight of N-(1-ethylpropyl)-N-nitroso-2,6-dinitro-3,4-xylidine.

EXAMPLE 7

Denitrosation of 3-Pentylphenylnitrosamine with Diethyl Ketone

A glass pressure reactor is charged with ethylene dichloride (15 ml), 3-pentylphenylnitrosamine (1.92 g), concentrated hydrochloric acid (2.94 g) and diethyl ketone (0.95 g), and the reactor is then sealed. The reaction mixture is heated to 85°–90° C. and stirred for 4 hours while the temperature is maintained at 85°–90° C. The reactor is then cooled down and vented. Examination of the reaction mixture by thin-layer chromatography (tlc) indicated no starting material to be present. The free amine (3-pentylaniline) is isolated from the reaction mixture and identified by tlc and nmr (nuclear magnetic resonance).

EXAMPLE 8

Denitrosation of N-(1-Ethylpropyl)-N-nitroso-2,6-dinitro-3,4-xylidine with cyclohexanone A glass pressure vessel is charged with an ethylene dichloride solution (19.2 g) containing N-(1-ethylpropyl)-2,6-dinitro-3,4-xylidine (33.8% by weight) and N-(1-ethylpropyl)-N-nitroso-2,6-dinitro-3,4-xylidine (11.7% by weight), concentrated hydrochloric acid (2.94 g) and cyclohexanone (1.0 g), and the reactor is then sealed. The reaction mixture is heated to 80°–85° C. over 30 minutes and stirred for 4 hours while the temperature is maintained at 80°–85° C. At the end of the reaction, the reactor is cooled and vented. Thin-layer chromatography of the crude reaction mixture indicates that the reaction is complete. The reaction mixture is adjusted to pH 10 and 12% sodium hydroxide and filtered. The filter cake is washed several times with ethylene dichloride. Analysis of the organic layer indicates the presence of 0.075% by weight of N-(1-ethylpropyl)-N-nitroso-2,6-dinitro-3,4-xylidine.

EXAMPLE 9

Denitrosation of N-(1-Ethylpropyl)-N-nitroso-2,6-dinitro-3,4-xylidine with acetone A glass pressure reactor is charged with an ethylene dichloride solution (96.0 g) containing N-(1-ethylpropyl)-2,6-dinitro-3,4-xylidine (39.6% by weight) and N-(1-ethylpropyl)-N-nitroso-2,6-dinitro-3,4-xylidine (13.4% by weight), concentrated hydrochloric acid (14.7 g) and acetone (2.50 g), and the reactor is then sealed. The reaction mixture is heated to 65°–70° C. and stirred 6 hours while the temperature is maintained at 65°–70° C. At the end of the reaction, the reactor is cooled down and vented. The reaction mixture is adjusted to pH 10 with 12% sodium hydroxide and filtered. The filter cake is washed several times with ethylene dichloride. The organic layer is separated, the aqueous layer is extracted with ethylene dichloride (50 ml). The organic layers are combined and the solvent evaporated under reduced pressure to afford 53.4 g solid which contains 92.3% by weight of N-(1-ethylpropyl)-2,6-dinitro-3,4-xylidine and 0.4% by weight of N-(1-ethylpropyl)-N-nitroso-2,6-dinitro-3,4-xylidine.

EXAMPLE 10

Preparation of N-(1-Ethylpropyl)-2,6-dinitro-3,4-xylidine

To a solution of mixed acid prepared by adding 70.5% nitric acid (145.2 g, 1.625 mol) and 94.5% sulfuric acid (116.6 g, 1.12 mol) to water (58.8 g), a solution of 94.6% N-(1-ethylpropyl)-3,4-xylidine (101.0 g, 0.5 mol) in ethylene dichloride (143.5 ml) is added over a period of 2 hours at 35° C. The reaction is maintained at 35° C. for one hour, and the aqueous phase is then separated. The organic phase is washed successively with 300 ml of 5% sodium hydroxide, and 300 ml of water. The organic solution is dried over anhydrous magnesium sulfate, filtered and concentrated under vacuum at 70° C. to afford 141.5 g solid containing 117.0 g (72.6%) N-(1-ethylpropyl)-2,6-dinitro-3,4-xylidine and 14.2 g (10%) N-nitroso-N-(1-ethylpropyl)-2,6-dinitro-3,4-xylidine.

EXAMPLE 11

Denitrosation of N-(1-Ethylpropyl)-N-nitroso-3,4-dimethylcyclohexylamine with diethyl ketone A glass pressure reactor is charged with ethylene dichloride (18.9 g), N-(1-ethylpropyl)-N-nitroso-3,4-dimethylcyclohexylamine (2.26 g), concentrated hydrochloric acid (2.75 g) and diethyl ketone (0.86 g) and the reactor is then sealed. The reaction mixture is heated to 85°–90° C. and stirred 4 hours while the temperature is maintained at 85°–90° C. At the end of the reaction, the reactor is cooled down and vented. The product, after washing the reaction mixture with water and 5% caustic soda solution and stripping free of solvent is primarily N-(1-ethylpropyl)cyclohexylamine.

EXAMPLE 12

Preparation and Denitrosation of N-(2-Pentyl)-N-nitroso-2,6-dinitro-3-methoxymethyl-4-ethylaniline N-(2-Pentyl)-3-methoxymethyl-4-ethylaniline (2.5 kg) dissolved in ethylene dichloride (1.73 liters) is allowed to react with a mixture of 70% nitric acid (4.48 kg), 96% sulfuric acid (3.57 kg) and water (1.64 kg) at 50° C. The product, dissolved in solvent, is a mixture of N-(2-pentyl)-2,6-dinitro-3-methoxymethyl-4-ethylaniline and its N-nitroso derivative.

A glass pressure reactor is charged with a portion of the above-described solution (96 g), concentrated hydrochloric acid (14.7 g) and diethyl ketone (5.0 g). The reactor is sealed and the mixture heated to 85°–90° C. It is stirred 4 hours while the temperature is maintained at 85°–90° C. At the end of the reaction, the reactor is cooled down and vented. The product, after washing the reaction mixture with water, with dilute caustic soda (to pH 9–10), and stripping free of solvent by distillation, is N-(2-pentyl)-2,6-dinitro-3-methoxymethyl-4-ethylaniline (46.98 g). It is substantially free of the N-nitroso analog, as shown by tlc and nmr.

We claim:

1. A method for the denitrosation of N-nitroso compounds of formula:

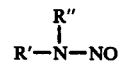

wherein R' represents alkyl $C_1$–$C_{12}$, cycloalkyl $C_4$–$C_8$, halo-alkyl $C_1$–$C_{10}$, alkoxy($C_1$–$C_6$)alkyl ($C_1$–$C_8$), phenyl or substituted phenyl wherein the substituents are halogen, alkyl $C_1$–$C_4$, alkoxy $C_1$–$C_4$, trifluoromethyl, alkoxy($C_1$–$C_4$)alkyl($C_1$–$C_4$) or nitro; R" represents alkyl $C_1$–$C_8$, cycloalkyl $C_4$–$C_8$, monohaloalkyl $C_1$–$C_6$ or alkoxy($C_1$–$C_4$)alkyl($C_1$–$C_4$); comprising reacting a nitroso compound of the above formula with a ketone or aldehyde represented by the formulae;

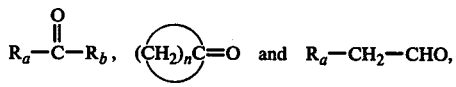

wherein $R_a$ represents lower alkyl, phenyl, or substituted phenyl, and $R_b$ represents lower alkyl; and n is an integer of 3 to 7; in the presence of hydrochloric or hydrobromic acid and optionally an inert organic solvent at atmospheric to superatmospheric pressures in the temperature range of from 20° C. to 120° C., for a period of time sufficient to essentially complete the reaction.

2. A method according to claim 1, wherein the N-nitroso compound is represented by formula:

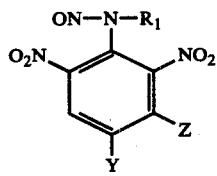

wherein $R_1$ represents alkyl $C_1$–$C_6$, cycloalkyl $C_4$–$C_6$, monohaloalkyl $C_1$–$C_4$ or alkoxy($C_1$–$C_4$)alkyl($C_2$–$C_4$); Y represents alkyl $C_1$–$C_4$, halogen or $CF_3$; Z represents hydrogen, halogen, alkyl $C_1$–$C_4$, alkoxy $C_1$–$C_4$, monohaloalkyl $C_1$–$C_4$ or alkoxy($C_1$–$C_4$)alkyl($C_2$–$C_4$).

3. A method according to claim 2, wherein the ketones and aldehydes are acetone, methyl ethyl ketone, diethyl ketone, dipropyl ketone, cyclohexanone, acetaldehyde, propionaldehyde or butyraldehyde in a ratio of 0.5 to 2.0 moles per mole of the N-nitroso compound, the inert solvent is chloroform, carbon tetrachloride, ethylene dichloride, toluene or xylene; the strong acid is hydrochloric acid or hydrobromic acid in a ratio of 0.5 to 10.0 moles of acid per mole of the N-nitroso compound, and the reaction is run at atmospheric to 40 psig superatmospheric pressure in the temperature range of 50° C. to 120° C.

4. A method according to claim 3, wherein the N-nitroso compound is N-(1-ethylpropyl)-N-nitroso-2,6-dinitro-3,4-xylidine, the ketones and aldehydes are acetone, diethyl ketone, cyclohexanone or propionaldehyde, the inert solvent is ethylene dichloride, and the strong acid is hydrochloric acid.

5. A method according to claim 4, wherein the ratio of the ketones and aldehydes is 0.75 to 1.5 moles per mole of the nitroso compound, the ratio of hydrochloric acid is 2 to 6 moles per mole of the nitroso compound, the inert solvent is ethylene dichloride, and the temperature range of the reaction is from 80° C. to 110° C.

6. A method according to claim 5 wherein the ketone acetone is used.

7. A method according to claim 5 wherein the ketone diethyl ketone is used.

8. A method according to claim 5 wherein the ketone cyclohexanone is used.

9. A method according to claim 5 wherein the aldehyde propionaldehyde is used.

* * * * *